United States Patent [19]

Brudermueller et al.

[11] Patent Number: 5,380,918
[45] Date of Patent: Jan. 10, 1995

[54] PREPARATION OF 4-ACETOXYSTYRENE

[75] Inventors: Martin Brudermueller, Mannheim; Franz Merger, Frankenthal, both of Germany

[73] Assignee: BASF Aktiengesellschaft, Ludwigshafen, Germany

[21] Appl. No.: 126,880

[22] Filed: Sep. 27, 1993

[30] Foreign Application Priority Data

Oct. 1, 1992 [DE] Germany .................. 4233039

[51] Int. Cl.⁶ ............................ C07C 67/297
[52] U.S. Cl. .................................. 560/130
[58] Field of Search ........................ 560/130

[56] References Cited

U.S. PATENT DOCUMENTS

| | | |
|---|---|---|
| 2,276,138 | 3/1942 | Alderman et al. |
| 4,927,956 | 4/1990 | Vicari et al. ............ 560/130 |
| 5,041,614 | 8/1991 | Aslam et al. |
| 5,151,546 | 9/1992 | Shah et al. ............. 560/130 |
| 5,194,672 | 3/1993 | Aslam et al. ............ 56/130 |
| 5,245,074 | 9/1993 | Shah et al. ............. 560/130 |

FOREIGN PATENT DOCUMENTS 355983 2/1990 European Pat. Off.

OTHER PUBLICATIONS

J. Org. Chem. 23(1958), 544–549.

Primary Examiner—José G. Dees
Assistant Examiner—Samuel Barts
Attorney, Agent, or Firm—Keil & Weinkauf

[57] ABSTRACT

4-Acetoxystyrene of the formula I

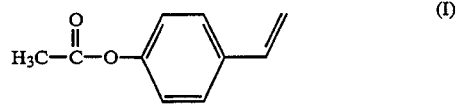

is prepared by a process in which a 1-(4-acetoxyphenyl)ethyl carboxylate of the formula II

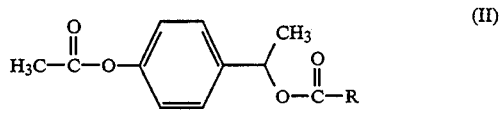

where R is $C_1$–$C_{10}$-alkyl, $C_3$–$C_6$-cycloalkyl, aryl or $C_7$–$C_{10}$-aralkyl, is converted in the presence of an acidic catalyst and of a polymerization inhibitor in an inert heat transfer medium at from 160° to 250° C. and from 0.1 to 300 mbar.

8 Claims, No Drawings

PREPARATION OF 4-ACETOXYSTYRENE

The present invention relates to a process for the preparation of 4-acetoxystyrene from a 1-(4-acetoxyphenyl)ethyl carboxylate over an acidic catalyst in an inert heat-transfer medium in the presence of a polymerization inhibitor at elevated temperatures and reduced pressure.

The preparation of 4-hydroxystyrene by catalytic dehydrogenation of 4-hydroxyethylbenzene is disclosed in EP-A-128 984.

J. Org. Chem. 23 (1958), 544–549 describes the preparation of 4-acetoxystyrene from phenol in four process stages: acetylation of phenol to 4-hydroxyacetophenone, esterification to 4-acetoxyacetophenone, hydrogenation to 1-(4-acetoxyphenyl)ethanol and dehydration to 4-acetoxystyrene. The dehydration of 1-(4-acetoxyphenyl)ethanol is carried out in the gas phase over activated alumina at 350° C. or in the liquid phase in the presence of solid potassium bisulfate.

However, particularly when carried out on an industrial scale, both processes lead to low yields owing to a high tendency of the product to polymerize and are therefore uneconomical.

EP-A-355 983 describes the preparation of 4-acetoxystyrene by dehydration of 1-(4-acetoxyphenyl)ethanol in a thin-film evaporator while maintaining very short residence times. In the presence of polymerization inhibitors and catalytic amounts of potassium bisulfate, incomplete conversions and unsatisfactory yields are obtained.

The coating of the reactor surface with the polymers, which occurs in the continuous operation of the reactor, cannot be effectively prevented and therefore does not permit the economical use of the process.

A further disadvantage of all processes described to date for the dehydration of 1-(4-acetoxyphenyl)ethanol is that the reaction mixtures discharged consist of two phases owing to the formation of stoichiometric amounts of water. The inhomogeneity of the reaction mixtures causes problems when carrying out the reaction.

U.S. Pat. No. 5,041,614 describes the dehydration of 1-(4acetoxyphenyl)ethanol in the presence of carboxylic anhydrides, of a dehydration catalyst and of polymerization inhibitors.

The resulting water, which, inter alia, promotes the formation of byproducts, such as polymers, is suppressed by the addition of a carboxylic anhydride with formation of carboxylic acids.

As a result of this measure, however, the formation of polymeric byproducts cannot be prevented. Instead, high boiling residues accumulate in the reaction space. Accumulation of polymeric byproducts leads to a reduction in the yield of desired product and a decrease in the selectivity of 4-acetoxystyrene. The polymer products must therefore be removed continuously from the reactor at considerable expense in the course of the reaction.

Compared with the prior art, the process according to U.S. Pat. No. 5,041,614 is therefore more expensive in terms of apparatus and has no substantial advantages with regard to the yield of 4-acetoxystyrene achieved.

The thermal cleavage of 1-(4-acetoxyphenyl)ethyl acetate (APEA) to give 4-acetoxystyrene in the gas phase at about 480° C. is disclosed in U.S. Pat. No. 2,276,138. The preparation of APEA is carried out by esterifying 1-(4-acetoxyphenyl)ethanol with acetyl chloride.

Owing to the formation of polymeric tar-like byproducts, the yield remains at the low level of about 50%. The process therefore likewise could not be used in industry.

It is an object of the present invention to remedy the abovementioned disadvantages.

We have found that this object is achieved by a novel and improved process for the preparation of 4-acetoxystyrene of the formula I

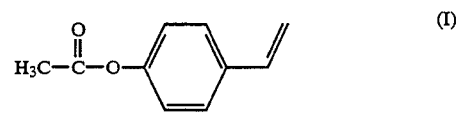

wherein a 1-(4-acetoxyphenyl)ethyl carboxylate of the general formula II

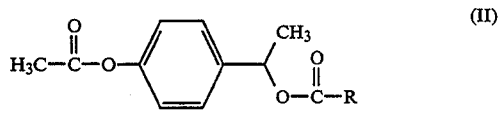

where R is $C_1$-$C_{10}$-alkyl, $C_3$-$C_6$-cycloalkyl, aryl or $C_7$-$C_{10}$-aralkyl, is converted in the presence of an acidic catalyst and a polymerization inhibitor in an inert heat transfer medium at from 160° to 250° C. and from 0.1 to 300 mbar.

The novel process can be carried out as follows: The 1-(4-acetoxyphenyl)ethyl carboxylate II can be reacted in pure forth, if necessary as a melt, or in the form of a solution in an inert solvent, preferably in a solution, obtained in the esterification, in the corresponding carboxylic acid, in the liquid phase, preferably in an inert heat transfer medium, at from 160° to 250° C., preferably from 180° to 210° C., and from 0.1 to 300, preferably from 1 to 100, particularly preferably from 5 to 80, mbar, in the presence of an acidic catalyst and of a polymerization inhibitor.

The acidic catalyst as well as the polymerization inhibitors can be initially taken in the inert heat transfer medium or can be added to the reaction mixture continuously or batchwise in the course of the reaction.

The reaction is advantageously carried out in a reaction kettle having an attached distillation column. It is advantageous initially to take the inert heat transfer medium, the cleavage catalyst and the polymerization initiator in the reaction kettle and to preheat the mixture to the reaction temperature. After the operating pressure has been established by means of a connected reduced pressure system at the top of the column, the carboxylate is metered in continuously or semicontinuously. A single-phase mixture of 4-acetoxystyrene and carboxylic acid is removed in gaseous form at the same rate at the top of the column and is condensed in a receiver.

When the product is metered into the liquid reaction medium, preferably via an immersion tube, by choosing the reaction pressure, the temperature and the reflux ratio in the continuous distillation of 4-acetoxystyrene from the reaction mixture it is possible, with a high space-time yield, to keep the steady-state concentration of starting material and product so low that secondary reactions, such as the formation of polymers, are substantially suppressed.

In the batchwise procedure, the inert heat transfer medium with the polymeric byproducts dissolved homogeneously therein can be disposed of after the end of the reaction or the inert heat transfer medium can be separated off by distillation and reused. In the continuous procedure, some of the heat transfer medium is removed continuously and is replaced by fresh heat transfer medium, in order to keep the polymer content at a low level.

Suitable 1-(4-acetoxyphenyl)ethyl carboxylate II are esters of 1-(4-acetoxyphenyl)ethanol with aliphatic or aromatic carboxylic acids which can be distilled off in free form under the reaction conditions and can be separated from the product acetoxystyrene by fractional distillation, preferably acetic acid and propionic acid, butyric acid, isobutyric acid and benzoic acid, and substituted carboxylic acids, such as methoxyacetic acid. The ester of acetic acid is particularly preferred.

The esters can be prepared in a known manner by reacting 1-(4-acetoxyphenyl)ethanol with carboxylic acids or with the anhydrides or chlorides of the stated acids (Organikum, VEB Deutscher Verlag der Wissenschaften, 981, pages 498–505).

Suitable inert heat transfer media are inert high-boiling heat transfer media, such as industrial oils having a boiling range above that of 4-acetoxystyrene, for example gas oil, vacuum oil, fuel oil, industrial white oil, mineral oils, molten paraffin wax, silicone oil or alkylaromatics, e.g. dodecylbenzene. Other liquids or mixtures which are inert under the reaction conditions and have a sufficiently low viscosity capable of ensuring good stirrability at the reaction temperature can also be used. Fuel oils which, through their continuous metering and removal from the reaction space, permit the continuous withdrawal of polymers at a low concentration and, together with them, can be used for energy generation are particularly preferred. The withdrawal of the polymers at relatively low concentration, based on the heat transfer medium in the reactor, ensures constant good yields of 4-acetoxystyrene.

Suitable polymerization inhibitors are commercially available compounds, for example tert-butylpyrocatechol, hydroquinone, hydroquinone monomethyl ether or phenothiazine, preferably mixtures of phenothiazine and hydroquinone monomethyl ether, which are added in a concentration of from 0.01 to 5% by weight, based on the inert heat transfer medium. The inhibitor may be initially taken in the inert heat transfer medium or can be metered in continuously with the starting material.

Suitable acidic catalysts are oxidic solid catalysts, for example alumina, silica gel, titanium oxide, zeolites and/or heteropoly acids, in concentrations of from 0.1 to 50, preferably from 3 to 10, % by weight, based on the inert transfer medium.

The acidic catalysts may be used in the form of tablets, chips or, preferably, powder. The use in the form of a powder is technically advantageous, so that the catalyst is present as a suspension in the inert heat transfer medium.

Other suitable catalysts are organic acids, for example p-toluenesulfonic acid, or mineral acids.

Oxidic solid catalysts can be separated off from the inert heat transfer medium and, in the case of declining activity, can be regenerated by a thermal treatment at from 350° to 500° C. and recycled to the reaction.

In compound II, R is $C_1$–$C_{10}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl or isodecyl, preferably $C_1$–$C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl or isooctyl, particularly preferably $C_1$–$C_4$-alkyl, such as methyl, ethyl, n-propyl, isopropyl, n-butyl, isobutyl, sec-butyl or tert-butyl, $C_3$–$C_6$-cycloalkyl, such as cyclopropyl, cyclobutyl, cyclopentyl or cyclohexyl, preferably cyclopentyl or cyclohexyl, aryl, such as phenyl, 1-naphthyl or 2-naphthyl, preferably phenyl, or $C_7$–$C_{10}$-aralkyl, preferably $C_7$–$C_{10}$-phenylalkyl, such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, 1-phenethyl or 2-phenethyl.

Polymers of acetoxystyrenes and hydroxystyrenes are used, inter alia, in adhesives, coatings and in particular photoresist films (cf. for example J. Photopolym. Sci. Technol. 3 (1990), 347).

EXAMPLES

The Examples below were carried out in an apparatus which consisted of a heated stirred flask having an attached column and condenser as well as a distillate receiver with a connection to a vacuum pump for obtaining the desired pressure in a controlled manner, metering of the starting material via the pump and an immersion tube into the liquid phase of the reaction space.

Example 1

300 g of Marlotherm oil, 45 g of $Al_2O_3/SiO_2$ powder (80% by weight/20% by weight), 3 g of phenothiazine and 3 g of hydroquinone monomethyl ether were initially taken in a 500 ml round-bottom flask with a distillation column. At an oil temperature of 200° C. and a pressure of 14 mbar, a melt comprising 215 g of 1-(4-acetoxyphenyl)ethyl acetate (APEA) (81% by weight of APEA and 19% by weight of acetic acid) was metered into the hot oil in the course of 2 hours, and 177 g of a single-phase distillate having the following composition were condensed continuously at about 100° C. at the top of the column:

23.7% by weight of acetic acid,
61.1% by weight of 4-acetoxystyrene,
1.0% by weight of 4-hydroxystyrene and
10.7% by weight of 1-(4-acetoxyphenyl)ethyl acetate The yield of 4-acetoxystyrene was 85% at a conversion of 89%, based on APEA (selectivity 95%).

Examples 2 to 4

The procedure was similar to Example 1.
The results are shown in the Table below.

TABLE

| Catalyst | Reaction temp. [°C.] | Pressure [mbar] | Metering [ml/min] | Yield [%] | Conversion [%] | Selectivity [%] |
|---|---|---|---|---|---|---|
| $Al_2O_3/SiO_2$ | 230 | 27 | 0.7 | 80.0 | 96.0 | 83.3 |

TABLE-continued

| Catalyst | Reaction temp. [°C.] | Pressure [mbar] | Metering [ml/min] | Yield [%] | Conversion [%] | Selectivity [%] |
|---|---|---|---|---|---|---|
| (80/20) 10% by weight Al$_2$O$_3$/SiO$_2$ (80/20) | 210 | 18 | 0.7 | 84.3 | 95.1 | 88.7 |
| 10% by weight Al$_2$O$_3$/SiO$_2$ (80/20) 10% by weight | 180 | 10 | 0.7 | 75.1 | 79.2 | 94.8 |

Example 5

400 g of Marlotherm oil, 30 g of Al$_2$O$_3$/SiO$_2$ powder (80% by weight/20% by weight), 2.5 g of phenothiazine and 2.5 g of hydroquinone monomethyl ether were initially taken in a 500 l round-bottom flask with a distillation column. At an oil temperature of 200° C. and a pressure of 11 mbar, 5 fractions each of 180 g of 1-(4-acetoxyphenyl)ethyl acetate (59.7% by weight of crude APEA from the esterification in 36.7% by weight of acetic acid) were each metered in the course of from 3 to 4 hours into hot oil (from 0.9 to 1.2 g/min). The distillate of each fraction was collected separately and analysed:

| Distillate | Yield of 4-acetoxystyrene [%] | Conversion [%] |
|---|---|---|
| 1 | 87.0 | 88.3 |
| 2 | 85.3 | 88.1 |
| 3 | 79.4 | 81.4 |
| 4 | 75.2 | 78.1 |
| 5 | 72.6 | 75.6 |

Comparative Examples with 1-(4-acetoxyphenyl)ethanol

EXAMPLE A 400 g of Marlotherm oil, 20 g of potassium bisulfate and 4 g of 3,5-di-tert-butylpyrocatechol were initially taken in a 250 ml stirred flask with a distillation column and a magnetic stirrer. At from 220° to 230° C./20mbar, 2.8 g/h of 1-(4-acetoxyphenyl)ethanol were metered in over 1 hour and 122.8 g of a two-phase distillate were taken off at a top temperature of 160° C. The organic phase (105.6 g) had the following composition:

71.5% of 4-acetoxystyrene and
15.7% of 1-(4-acetoxyphenyl)ethanol.

A viscous residue remained in the bottom. The yield of 4-acetoxystyrene is 49%.

EXAMPLE B

In a 500 ml stirred flask having a 30 cm long distillation column, 200 g of mineral oil, 20 g of dodecylsulfonic acid and 2 g of 3,5-di-tert-butyl-pyrocatechol were heated at 230° C. at 0.3 mbar. 115 g of 1-(4-acetoxyphenyl)ethanol were metered in over 2 hours, and a two-phase distillate consisting of 69 g of organic phase and 11 g of water was distilled off continuously at from 67° to 70° C. The organic phase had the following composition:

47.8% of 4-acetoxystyrene,
19.3% of 4-hydroxystyrene and
14.8% of 1-(4-acetoxyphenyl)ethanol.

A yield of 4-acetoxystyrene was 32%.

We claim:

1. A process for the preparation of 4-acetoxystyrene of the formula I

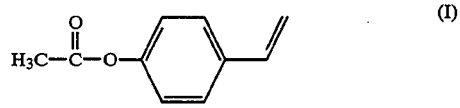

wherein a 1-(4-acetoxyphenyl)ethyl carboxylate of the formula II

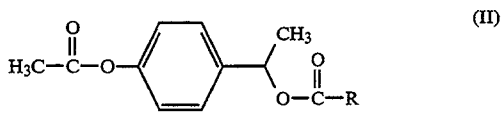

where R is C$_1$–C$_{10}$-alkyl, C$_3$–C$_6$-cycloalkyl, aryl or C$_7$–C$_{10}$-aralkyl, is converted in the presence of an acidic catalyst and of a polymerization inhibitor in an inert high boiling transfer medium at from 160° to 250° C. and from 0.1 to 300 mbar.

2. A process for the preparation of 4-acetoxystyrene I as claimed in claim 1, wherein acetoxystyrene is isolated during the reaction by distillation from the synthesis gas.

3. A process for the preparation of 4-acetoxystyrene I as claimed in claim 1, wherein a technical oil is used as an inert heat transfer medium.

4. A process for the preparation of 4-acetoxystyrene I as claimed in claim 1, wherein a mineral oil, white oil or silicone oil is used as the inert heat transfer medium.

5. A process for the preparation of 4-acetoxystyrene I as claimed in claim 1, wherein the acidic catalyst used is an oxidic solid catalyst.

6. A process for the preparation of 4-acetoxystyrene I as claimed in claim 1, wherein the acidic catalyst used is alumina, silica, titanium oxide, zirconium oxide or a zeolite.

7. A process for the preparation of 4-acetoxystyrene I as claimed in claim 1, wherein 1-(4-acetoxyphenyl)ethyl acetate or a solution of 1-(4-acetoxyphenyl)ethyl acetate in acetic acid is used.

8. A process for the preparation of 4-acetoxystyrene I as claimed in claim 1, wherein the polymerization inhibitor used is a mixture of hydroquinone monomethyl ether and phenothiazine.

* * * * *